United States Patent [19]

Blank et al.

[11] 4,393,234

[45] Jul. 12, 1983

[54] PROCESS FOR THE PREPARATION OF 3-HYDROXYBENZOIC ACID

[75] Inventors: Heinz U. Blank, Odenthal; Eike Gabel, Bergisch-Gladbach; Ernst Goldschmitt, Dormagen; Werner Mentzel, Cologne, all of Fed. Rep. of Germany

[73] Assignee: Bayer Aktiengesellschaft, Leverkusen, Fed. Rep. of Germany

[21] Appl. No.: 378,922

[22] Filed: May 17, 1982

[30] Foreign Application Priority Data

Jun. 4, 1981 [DE] Fed. Rep. of Germany ....... 3122260
Jun. 4, 1981 [DE] Fed. Rep. of Germany ....... 3122264

[51] Int. Cl.$^3$ .............................................. C07C 65/04
[52] U.S. Cl. ..................................... 562/475; 562/429
[58] Field of Search ........................................ 562/475

[56] References Cited

FOREIGN PATENT DOCUMENTS 11815 11/1979 European Pat. Off. .
48-72146 9/1973 Japan .................................... 562/475
48-72147 9/1973 Japan .................................... 562/475
1101267 1/1968 United Kingdom ................ 562/475

OTHER PUBLICATIONS

Lieb. Ann. Chem. 280, 6, (1894).

J. Chem. Soc., 1950, 2,108.

Primary Examiner—Paul J. Killos
Attorney, Agent, or Firm—Sprung, Horn, Kramer & Woods

[57] ABSTRACT

3-Hydroxybenzoic acid is obtained by reaction with an alkali metal hydroxide at a temperature of 220° to 450° C. and under a pressure of 1 to 120 bars, from a technical 3-sulphobenzoic acid mixture which contains sulphuric acid and/or sulphur trioxide and which contains at least 75% by weight of 3-sulphobenzoic acid, relative to the total organic constituents present, and not more than 35% by weight of sulphuric acid and/or $SO_3$, relative to the total mass. For this purpose, this technical 3-sulphobenzoic acid mixture, if desired after dilution with an equal volume of water, is mixed with sufficient 50 to 100% strength by weight alkali metal hydroxide wherein the remaining 50 to 0% by weight consists essentially of water, for 2.5 to 8 mols of alkali metal hydroxide to be present per mol of 3-sulphobenzoic acid, after neutralization of the sulphuric acid and all the sulpho and carboxyl groups. In general, 10 to 45% by weight of water are present in the batch. The reaction mixture is acidified with a mineral acid to a pH value of less than 4, if appropriate after dilution with water, and the 3-hydroxybenzoic acid is isolated at temperatures within the range from $-5°$ C. to $+40°$ C.

28 Claims, No Drawings

PROCESS FOR THE PREPARATION OF 3-HYDROXYBENZOIC ACID

The present invention relates to a process for the preparation of 3-hydroxybenzoic acid from a technical sulphonation mixture containing 3-sulphobenzoic acid.

It is known to prepare 3-hydroxybenzoic acid from 3-sulphobenzoic acid by means of an alkali metal hydroxide fusion, the sulpho group being replaced by a hydroxyl group. What is employed for the alkali fusion is, in general, the monosodium salt of 3-sulphobenzoic acid, which is obtained by sulphonating benzoic acid with 2.6 mols of $SO_3$, in the form of 20% strength oleum, per mol of benzoic acid, diluting the sulphonation mixture with water, neutralizing it partially with sodium hydroxide solution or salting out with sodium chloride, filtering off the product and drying it (Lieb, Ann. Chem. 280, 6 (1894)). J. Chem. Soc. 1950, 2,108 describes the improvement of a fusion process with potassium hydroxide which has been known for a long time, in which improvement the monosodium salt of 3-sulphobenzoic acid is triturated with 50% strength aqueous sodium hydroxide solution and the mixture is dried and fused, in the form of this mixed fusion mass, with potassium hydroxide.

It is known from U.S. Pat. No. 3,094,558 that the use of the expensive potassium hydroxide solution can be replaced by sodium hydroxide with equally good yields, if the reaction is carried out in the presence of small quantities of water.

In all the processes hitherto known, it has been considered necessary to isolate intermediately the 3-sulphobenzoic acid in the form of its monosodium salt, because that salt can be mixed, as a solid in a simple and easily controlled manner, with the alkali metal hydroxide and because a purification is carried out at the same time as the intermediate isolation, in which, above all, sulphuric acid from the excess sulphonation reagent and a fraction of the by-products which are inevitable in any sulphonation reaction carried out by an economical sulphonation process, for example 2-sulphobenzoic acid, 4-sulphobenzoic acid and other organic by-products, remain in solution in the mother liquor.

However, this use of the monosodium salt of 3-sulphobenzoic acid in the processes described has the following disadvantages:
1. An additional process stage is required;
2. The intermediate isolation and drying occasion the use, and subsequent evaporation, of large quantities of water, with a corresponding outlay of energy;
3. Considerable quantities of 3-sulphobenzoic acid remain in the mother liquor and thus reduce the total yield;
4. The intermediate isolation process gives rise to the discharge of an effluent which, in the case of partial neutralization and particularly in the case of salting out with sodium chloride, contains considerable quantities of sulphuric acid (dilute acid);
5. The heat energy contained in the crude mixture from the sulphonation of benzoic acid, and, particularly, also the potential chemical energy liberated, for example, by neutralization, is completely lost.

SUMMARY OF INVENTION

A process has now been found for the preparation of 3-hydroxybenzoic acid by reacting 3-sulphobenzoic acid with an alkali metal hydroxide at elevated temperatures and, if desired, elevated pressure, which is characterized in that
(a) a technical 3-sulphobenzoic acid mixture containing sulphuric acid and/or sulphur trioxide, which contains at least 75% by weight of 3-sulphobenzoic acid, relative to the total organic constituents present and not more than 35% by weight of sulphuric acid and/or $SO_3$, relative to the total mass, is employed in the reaction,
(b) this mixture, if desired, as an aqueous solution, is mixed at elevated temperature and, if desired, elevated pressure, with sufficient 50 to 100% strength by weight alkali metal hydroxide wherein the remaining 50 to 0% by weight consists essentially of $H_2O$, for 2.5 to 8 mols of alkali metal hydroxide to be present per mol of 3-sulphobenzoic acid, after neutralization of the sulphuric acid and all the sulpho and carboxyl groups,
(c) the alkaline reaction mixture is reacted at temperatures within the range from 220° to 450° C. and under a pressure of 1 to 120 bars, if appropriate sufficient water is added under pressure for 10 to 45% by weight of water to be present in the mixture, and
(d) the alkaline reaction mixture, if desired, after dilution with water, is acidified with mineral acids to a pH value less than 4 and the 3-hydroxybenzoic acid is then isolated at temperatures within the range from −5° C. to +40° C.

The process can be performed without intermediate isolation of the mono-sodium or potassium salts of 3-sulphobenzoic acid. Moreover, the process can be performed without intermediate removal of sulfuric acid.

The technical sulphonation mixtures which can be employed in accordance with the invention have, for example, the following composition: 70 to 95% by weight of 3-sulphobenzoic acid, 2.5 to 7% by weight of 4-sulphobenzoic acid, 0.5 to 1.5% by weight of 2-sulphobenzoic acid, 0.01 to 0.5% by weight of 3,5-disulphobenzoic acid, 0.01 to 1.5% by weight of diphenyl sulphone derivatives, 0.01 to 1.5% by weight of benzophenone derivatives and 2.0 to 20% by weight of $SO_3$ (in the form of $SO_3$ and/or $H_2SO_4$).

This technical sulphonation mixture can, if desired, be diluted with water up to equal parts.

Many of the known sulphonation processes produce 3-sulphobenzoic acid mixtures which contain a proportion of sulphonation reagents which is uneconomically high for the present process, or which are distinguished at least by an unfavourably high proportion of undesirable organic by-products.

Thus it is known to react benzoic acid with 6 times its weight of concentrated sulphuric acid in the presence of 10% by weight of mercury sulphate, relative to the benzoic acid, in a 45-hour reaction at 135° C. (Ber. dt. Chem. Ges. 40, 2,411 (1907)). The use of such large quantities of sulphonating reagents is unsatisfactory, since firstly an increased use of chemicals is required and, secondly, the reaction mixture is diluted in order to separate the 3-sulphobenzoic acid from the large quantity of excess sulphonation reagent and a fairly large quantity of sodium chloride is added in order to salt out the 3-sulphobenzoic acid, thus giving the dilute sulphuric acid containing salt (dilute acid) which can only be worked up industrially with extreme difficulty.

Besides the desired 3-sulphobenzoic acid, this sulphonation process and the sulphonation process already mentioned earlier in the text also produce the undesired isomers, namely 4-sulphobenzoic acid and 2-sulphobenzoic acid. In re-working this process, it has, furthermore, also been possible to detect 3,5-disulphobenzoic acid and also diphenyl sulphone and benzophenone derivatives. A considerable part of the benzoic acid employed is thus consumed in undesired side reactions. Removal of these by-products is extremely expensive and is associated with losses in the yield of 3-sulphobenzoic acid.

The reaction of benzoic acid with gasous sulphur trioxide is described in J. pr. Chemie (2) 143, 127 (1935), 3-sulphobenzoic acid being obtained, according to the data given, in a selectivity of 100%. In this reaction, however, only 80% of the sulphur trioxide required for complete conversion of the benzoic acid were added. This shows that undesired by-products are formed preferably at conversions higher than 80%. This variant is not suitable for an industrial process, since the separation of the excess benzoic acid can only be carried out in a troublesome manner and with considerable loss.

A further process for the preparation of 3-sulphobenzoic acid is described in Ind. Eng. Chem. 45, 2,065 (1953), in which the benzoic acid is mixed with liquid sulphur trioxide (1.1 mols of $SO_3$ per mol of benzoic acid employed) at a temperature of 125° to 140° C., and the subsequent reaction is carried out at 130° to 150° C. According to our own observations, the reaction is complete after 2 to 4 hours in this process. It is a disadvantage of this sulphonation process that a large part of the benzoic acid employed is consumed in the formation of undesired by-products.

It has now also been found that 3-sulphobenzoic acid mixtures which have a high content of 3-sulphobenzoic acid and, at the same time, a lower content of sulphuric acid or $SO_3$, and which are thus particularly suitable for use in the process according to the invention can be prepared if benzoic acid is mixed with 0.01–0.5 mol of sulphuric acid per mol of benzoic acid and is then sulphonated with $SO_3$ or oleum.

In the case of these sulphonation mixtures it is not necessary to separate the 3-sulphobenzoic acid from the excess sulphonation reagents. At the same time, the content of benzophenone derivatives in the sulphonation melt can be reduced by at least half the values in the process according to Ind. Eng. Chem. (loc. cit.), and the impurity in the product of the alkali fusion can thus be minimized.

Accordingly, a particular variant of the process according to the invention is characterized in that benzoic acid is mixed with 0.01 to 0.5 mol of sulphuric acid per mol of benzoic acid and is sulphonated at elevated temperature with 1 to 1.2 mols of $SO_3$, per mol of benzoic acid, in the form of gaseous $SO_3$ and/or liquid $SO_3$ which can contain 0 to 35% by weight of sulphuric acid, relative to the $H_2SO_4$—$SO_3$ mixture, and the resulting reaction mixture is subjected to the measures (b), (c) and (d) mentioned above.

In this process, the benzoic acid to be sulphonated is mixed with 0.01 to 0.5 mol, preferably 0.05 to 0.4 mol and particularly preferentially 0.1 to 0.3 mol, of sulphuric acid per mol of benzoic acid. The sulphonation reagent used can be gaseous and/or liquid sulphur trioxide. Liquid sulphur trioxide can also be employed in this process in the form of oleum. The sulphuric acid content in the liquid $SO_3$ may be quoted, in this connection, as, for example, a range from 0 to 35% by weight of sulphuric acid, relative to the $H_2SO_4$—$SO_3$ mixture.

The sulphonation is carried out at a temperature of, for example, 40° to 170° C. The benzoic acid/sulphuric acid mixture is mixed with the sulphonation reagent at a temperature of 40° to 140° C., preferably 40° to 125° C., and the reaction is then completed within the upper part of the temperature range mentioned, up to 170° C. The sulphonation can be carried out, for example, in the following variants:

1. The benzoic acid/sulphuric acid mixture is taken, at 40° to 125° C., in the form of an inhomogeneous mixture or a melt, and 1 to 1.2 mols of gaseous and/or liquid $SO_3$, in the case of liquid $SO_3$ preferably in the form of 100% strength $SO_3$, are added per mol of benzoic acid. If necessary, the temperature in this reaction is limited to a value below 125° C. by means of external cooling during mixing. The temperature should not be less than 40° C., in order to make adequate intermixing of the reaction mixture still possible. Good results are still achieved even above 125° C., but such temperatures during mixing are not preferred. The sulphonation is then completed at a temperature of 125° to 170° C. preferably 130° to 150° C.

2. Liquid sulphur trioxide or oleum is taken in the quantity indicated above and the solid or liquid benzoic acid/sulphuric acid mixture is introduced into it. At the start of the mixing process, the temperature is generally limited by the boiling point of sulphur trioxide, which is kept in the reaction mixture, for example, by means of total reflux. As the reaction proceeds, it is possible to achieve a higher temperature, in the range from 40° to 125° C., even during mixing. A temperature range which is particularly preferred for the mixing is 40° to 90° C. In this variant too, the sulphonation is completed at 125° to 170° C., preferably 130° to 150° C.

Sulphonation mixtures which can be prepared in accordance with these variants contain, for example, 64 to 93% by weight of 3-sulphobenzoic acid and not more than 35% by weight, preferably less than 25% by weight and particularly preferentially less than 15% by weight, of sulphuric acid/sulphur trioxide. The conversion in this reaction is generally more than 98% and is frequently over 99%. The yield of the components present in the sulphonation mixture, relative to the benzoic acid which has reacted is, for example, as follows:

|  | % of theoretical yield |
|---|---|
| 3-Sulphobenzoic acid | 88–95, preferably 92–95 |
| 4-Sulphobenzoic acid | 4–7, preferably 4–5.5 |
| 2-Sulphobenzoic acid | 0.8–1.5, preferably 0.8–1.3 |
| 3,5-Disulpho-benzoic acid | 0.01–0.5, preferably 0.01–0.3 |
| Benzophenone derivatives | 0.01–1.5, preferably 0.01–0.8 |
| Diphenyl sulphone derivatives | 0.01–1.5, preferably 0.01–1.0 |

These values denote, in particular, a higher content of 3-sulphobenzoic acid and a lower content of benzophenone derivatives, compared with previous sulphonation processes.

The reduction in the proportion of benzophenone derivatives is particularly advantageous if the 3-sulphobenzoic acid melt is to be directly processed further to give a particularly pure secondary product and if, at the same time, an expensive purification of the sulphonation melt is to be avoided.

For example, an unknown by-product which can only be removed with difficulty and which is probably formed, together with other products, from the benzophenone derivatives, is found in the 3-hydroxybenzoic acid resulting from the 3-sulphobenzoic acid obtained by the process in Ind. Eng. Chem. (loc. cit.) after the latter has been subjected to alkali fusion.

It is an essential characteristic of the process according to the invention that such sulphonation mixture are employed in a direct manner and without intermediate isolation of the 3-sulphobenzoic acid. The sulphonation mixture are mixed with 50 to 100% strength by weight alkali metal hydroxide wherein the remaining 50 to 0% by weight consists essentially of water. In addition, the alkali metal hydroxides or solutions thereof can also contain, for example, the small quantities of carbonates or bicarbonates which are present in technical solutions of alkali metal hydroxides. It is preferable to employ a 60 to 90% strength, particularly a 65 to 80% strength, alkali metal hydroxide. Examples of alkali metal hydroxides which may be mentioned are sodium hydroxide and potassium hydroxide, preferably sodium hydroxide. The quantities of alkali metal hydroxide are such that, after neutralization of the sulphuric acid and all the sulpho and carboxyl groups, 2.5 to 8 mols, preferably 3 to 6 mols, particularly preferentially 3.5 to 5.5 mols and very particularly preferentially 4 to 5 mols, of alkali metal hydroxide are present per mol of 3-sulphobenzoic acid.

In this process, the quantity of heat contained in the sulphonation mass is introduced into the following process stage and the energy which would otherwise have to be applied to warm up and melt the organic component, is saved. In mixing the technical 3-sulphobenzoic acid sulphonation mixture directly with an alkali metal hydroxide which optionally contains water, additional heat energy is produced from the reaction, in particular from the neutralization of excess sulphuric acid and the sulpho and carboxyl groups in the reaction mixture, as a result of which an extremely economical process for the preparation of 3-hydroxybenzoic acid is made available.

Technical 3-sulphobenzoic acid sulphonation melts can be mixed in various ways with an alkali metal hydroxide, optionally containing water, which has been warmed above its solidification point.

Thus, for example, the sulphonation melt, optionally diluted with water, or the alkali metal hydroxide can be taken initially and the appropriate other component can be metered in; preferably, the alkali metal hydroxide is initially taken. It is also possible, however, to feed both the components simultaneously to the mixing operation. The mixing can be carried out either under normal pressure or while simultaneously building up a pressure higher than atmospheric. In building up a higher pressure, this pressure can be limited to a previously fixed value, for example by blowing off steam. This concentrates the mixture at the same time. If the process is carried out under normal pressure and if the pressure is limited to a previously fixed value, a part of the heat of neutralization is removed, for example by means of a condenser or by blowing off steam. In every case, however, at least part of the heat of neutralization remains in the system and can be made use of advantageously for the subsequent pressure hydrolysis.

Amongst the variants of the mixing procedure which are possible by combining the parameters mentioned, the following examples may be described in greater detail:

1. The technical 3-sulphobenzoic acid melt, if desired diluted with water, but preferably undiluted, is, for example, metered into initially taken 60 to 90% strength sodium hydroxide solution which has been heated to the boil, in the course of which water is removed continuously by distillation without external application of heat and the batch thus becomes more concentrated. Distillation of water can, however, also follow the premixing.

2. The sulphobenzoic acid melt is pumped or injected under pressure, for example into previously taken molten 60 to 90% strength sodium hydroxide solution, in the course of which, merely by utilizing the heat thus liberated, the reaction temperature of, for example, 260° to 370° C. is reached, which is advantageous for the subsequent reaction to give 3-hydroxybenzoic acid. If it is intended to achieve, in this process variant, a limitation of the simultaneous increase in pressure, this can be effected by blowing off steam.

3. The technical 3-sulphobenzoic acid melt, preferably not diluted, and the concentrated aqueous sodium hydroxide solution are pumped simultaneously into a mixing tube, the mixing tube being so designed that complete mixing takes place solely as a result of the turbulent flow produced. If desired the mixing process can also be assisted by internal fitments in the mixing tube, but this measure is not absolutely necessary. For example, 2,000 to 5,000 ml per hour of technical sulphonation melt can be mixed with corresponding quantities of sodium hydroxide solution in a mixing tube 500 mm in length and 5 mm in diameter, and can be conveyed into the reaction vessel for the subsequent pressure hydrolysis. This variant also can be carried out under normal pressure or under an elevated pressure, this elevated pressure being limited, if desired. If the initial temperatures of the components are suitably chosen, for example 150° to 180° C. for the sulphonation melt and 100° to 180° C. for the sodium hydroxide solution, a reaction temperature which is advantageous for the reaction to give 3-hydroxybenzoic acid, for example 270° to 320° C., will be reached at the end of the mixing tube. It can also be advantageous to carry out the mixing operation at a lower temperature or to limit the resulting steam pressure by blowing off steam. This process constitutes a partially continuous process in which the mixing operation in the mixing tube constitutes the continuous part of the process and the subsequent completion of the reaction in an autoclave constitutes the discontinuous part. However, since the reaction between the 3-sulphobenzoic acid and the alkali metal hydroxide becomes increasingly rapid in the upper part of the temperature range of 220° to 450° C. mentioned, it is also possible to complete the conversion into 3-hydroxybenzoic acid and thus the total reaction in a continuous form in the mixing tube itself, if the temperature is sufficiently high, for example in the region of 400° C. and if the corresponding pressure is maintained.

If the continuous procedure in the mixing tube at a high temperature in the region of about 400° C., which has been mentioned in the previous paragraph, is not selected, in all the other variants of the process according to the invention the mixing of 3-sulphobenzoic acid melt with alkali metal hydroxide is advantageously followed by a pressure hydrolysis of the suspension then present to give the dialkali metal e.g. disodium salt of 3-hydroxybenzoic acid.

The temperature for this pressure hydrolysis is, for example, 220° to 450° C., preferably 260° to 370° C. The pressure can be 1 to 120 bars. Pressure hydrolysis is advantageously carried out under the autogenous steam pressure of the system or under a steam partial pressure of about 5 to about 80 bars, preferably 10 to 40 bars.

Higher concentrations of the alkali metal hydroxide employed and/or higher reaction temperatures accelerate the reaction to give 3-hydroxybenzoic acid. For example, a reaction time of about 15 minutes or less may be quoted for a temperature of 370° C. and an initial concentration of the alkali metal hydroxide e.g. sodium hydroxide solution of 80%, also a reaction time of about 4 hours at 290° C. and alkali metal hydroxide e.g. sodium hydroxide solution initially 80% in strength, also a reaction time of about 6 hours at 340° C. and alkali metal hydroxide e.g. sodium hydroxide solution initially 50% in strength. As already described above, however, at an even higher temperature and at very high concentrations of alkali metal hydroxide, the reaction time can be limited to a few minutes, so that the residence time in a mixing tube can be adequate for carrying out the pressure hydrolysis.

It is known from German Offenlegungsschrift 2,852,163 that 4-hydroxybenzoic acid and 2-hydroxybenzoic acid decarboxylate to give phenol in alkaline hydrolyses under pressure. This reaction also takes place under the reaction conditions of the process according to the invention. It has been found that the decarboxylation takes place particularly readily if the total water content of the batch is about 10 to 45% by weight, preferably 20 to 41% by weight. In order to complete the decarboxylation of the said hydroxybenzoic acid, it can, therefore, be advantageous to adjust the mixture to this concentration range by subsequent addition of water, unless this concentration range is established of itself as a result of mixing the sulphonation melt with the optionally aqueous alkali metal hydroxide. In contrast with 4-hydroxybenzoic acid and 2-hydroxybenzoic acid, and also in contrast with the 4-sulphobenzoic acid and 2-sulphobenzoic acid originally present, the phenol formed can be removed in a simple manner when the 3-hydroxybenzoic acid is isolated, since it remains in the mother liquor owing to its solubility.

The free 3-hydroxybenzoic acid is worked up and isolated by a customary method by acidification with a strong mineral acid, such as, for example, hydrochloric acid or sulphuric acid, after which the mixture is diluted with the quantity of water necessary to dissolve the inorganic salts, and the desired 3-hydroxybenzoic acid is precipitated in a high state of purity. The temperature is adjusted to about −5° C. to about +40° C., for example, for this precipitation.

In this connection, it has been found that particularly pure products, which are free from organic impurities, are obtained if the pH is adjusted to a value of about 0 to about 4, preferably 1 to 3 and particularly preferentially 2 to 2.8, for the isolation of the 3-hydroxybenzoic acid.

The process according to the invention is distinguished by particularly high yields of 3-hydroxybenzoic acid. If a technical 3-sulphobenzoic acid sulphonation mixture is used, the yield from the reaction, relative to the 3-sulphobenzoic acid present in the sulphonation mixture employed, is, surprisingly, 100 to 101%, even higher than if pure 3-sulphobenzoic acid is employed, in which case yields of 3-hydroxybenzoic acid of about 96 to 98% are achieved. Although this fact has not been explained completely, it can be assumed that diphenyl sulphone and benzophenone derivatives which can be present as minor constituents to the extent of up to 3% by weight in the 3-sulphobenzoic acid sulphonation mixture, are also reacted, together with the 3-sulphobenzoic acid, to give 3-hydroxybenzoic acid. Thus part of the benzoic acid originally employed for the sulphonation is also converted subsequently into the desired product, while in the case of processes of the state of the art which carry out an intermediate purification of the 3-sulphobenzoic acid, this advantageous conversion of by-products is excluded.

3-Hydroxybenzoic acid is an important intermediate product for the preparation of plant protection agents. Thus, in accordance with U.S. Pat. No. 4,031,131, 3-hydroxybenzoic acid can be reacted with 3,4-dichlorobenzotrifluoride in methanolic solution and in the presence of potassium hydroxide and dimethyl sulphoxide, to give 3-(2-chloro-4-trifluoromethylphenoxy)-benzoic acid. Nitrating this benzoic acid with potassium nitrate in concentrated sulphuric acid then gives 5-(2-chloro-4-trifluoromethylphenoxy)-2-nitrobenzoic acid which, according to U.S. Pat. No. 3,798,276, is an important herbicide.

EXAMPLE 1

(Preparation of a 3-sulphobenzoic acid mixture)

305 g (2.5 mols) of benzoic acid and 49 g (0.5 mol) of sulphuric acid are melted at 110° C. in a stirred vessel and 210 g (2.63 mols) of $SO_3$ are added in the form of gas, the temperature being limited to 120° C. by external cooling.

Stirring is continued for 4 hours at 140° C. in order to complete the reaction. This gives 559 g (99.2% of the total quantity of substances charged) of a 3-sulphobenzoic acid sulphonation mixture which, at 140° C., is present in the form of a viscous melt.

The melt contains:

| | | |
|---|---|---|
| 468 g of 3-sulphobenzoic acid | = | 92.6% of the theoretical yield |
| 24.8 g of 4-sulphobenzoic acid | = | 4.9% of the theoretical yield |
| 4.5 g of 2-sulphobenzoic acid | = | 0.9% of the theoretical yield |
| 1.9 g of benzophenone derivatives | = | 0.5% of the theoretical yield |
| 1.1 g of diphenyl sulphone derivatives | = | 0.3% of the theoretical yield |
| 2.4 g of unreacted benzoic acid | = | 0.8% of the benzoic acid employed |

EXAMPLE 2

305 g (2.5 mols) of benzoic acid and 25 g (0.25 mol) of sulphuric acid are mixed at room temperature in a stirred vessel. 220 g (2.75 mols) of liquid $SO_3$ are added dropwise, the temperature in the interior of the vessel being limited to 40°–70° C. by external cooling.

When the addition is complete, the mixture is heated to 140° C. in the course of 1 hour and is stirred for a further 3 hours.

The resulting melt contains:

| | | |
|---|---|---|
| 85% by weight of 3-sulphobenzoic acid | = | 92.5% of the theoretical yield |
| 4.3% by weight of 4-sulphobenzoic acid | = | 4.7% of the theoretical yield |

-continued

| | | |
|---|---|---|
| 1.0% by weight of 2-sulphobenzoic acid | = | 1.1% of the theoretical yield |
| 0.4% by weight of benzophenone derivatives | = | 0.6% of the theoretical yield |
| 0.2% by weight of diphenyl sulphone derivatives | = | 0.3% of the theoretical yield |
| 0.1% by weight of benzoic acid | = | 0.2% of the benzoic acid employed |

EXAMPLE 3

310 g of 65% strength oleum (2.52 mols of free $SO_3$) are placed in a stirred vessel at 40° C. and a liquid mixture consisting of 305 g (2.5 mols) of benzoic acid and 25 g (0.25 mol) of sulphuric acid is added at such a rate that the internal temperature does not increase above 90° C. The resulting, readily stirrable suspension is heated to 130° C. in the course of 1 hour and is stirred at that temperature for a further 4 hours. The melt contains:

| | | |
|---|---|---|
| 74.2% by weight of 3-sulphobenzoic acid | = | 94% of the theoretical yield |
| 3.2% by weight of 4-sulphobenzoic acid | = | 4.0% of the theoretical yield |
| 0.6% by weight of 2-sulphobenzoic acid | = | 0.8% of the theoretical yield |
| 0.4% by weight of benzophenone derivatives | = | 0.6% of the theoretical yield |
| 0.4% by weight of diphenyl sulphone derivatives | = | 0.6% of the theoretical yield |

EXAMPLE 4

(Preparation of a 3-sulphobenzoic acid mixture in accordance with Ind. Eng. Chem. 45. 2,065 (1953))

1,465 g (12 mols) of benzoic acid are melted at 125° C. in a stirred vessel and 1,056 g (13.2 mols) of liquid $SO_3$ are added dropwise, the internal temperature being limited to 130° C. After the addition, the internal temperature is increased to 140° C. and is kept at that figure for 4 hours. This gives 2,505 g (99.4% by weight of the total quantity of substances charged) of a melt of the following composition:

| | | |
|---|---|---|
| 88.0% by weight of 3-sulphobenzoic acid | = | 90.9% of the theoretical yield |
| 5.8% by weight of 4-sulphobenzoic acid | = | 6.0% of the theoretical yield |
| 1.0% by weight of 2-sulphobenzoic acid | = | 1.0% of the theoretical yield |
| 0.1% by weight of benzoic acid | = | 0.2% of the theoretical yield |
| 0.8% by weight of benzophenone derivatives | = | 1.1% of the theoretical yield |
| 0.5% by weight of diphenyl sulphone derivatives | = | 0.7% of the theoretical yield |

EXAMPLE 5

224 g of a 3-sulphobenzoic acid melt, prepared in accordance with Example 1, are melted in a dropping funnel.

400 g of 70% strength sodium hydroxide solution (=7.0 mols of NaOH), which is heated to 156° C. and is stirred vigorously, are placed in a glass flask equipped with a distillation apparatus.

The sulphobenzoic acid melt is added dropwise in the course of 15 minutes, in the course of which 63 ml of $H_2O$ are removed by distillation without further heat being applied.

The hot, readily stirrable suspension is transferred to a 0.7 l Ni stirred autoclave and is heated at 290° C. for 4 hours, a pressure of 22 bars being set up. The batch is diluted with 520 ml of $H_2O$ and is acidified to pH 2 with 37% strength hydrochloric acid. The product, which has been precipitated and filtered off at 20° C., is washed with water until it is free from salt and is dried in vacuo. This gives 126.7 g of 99% pure 3-hydroxybenzoic acid=98% of the theoretical yield, relative to 3-sulphobenzoic acid, or 91% of the theoretical yield, relative to benzoic acid employed.

Further Examples 5a–5f, using various reaction conditions, are listed in the following table.

| Example | Sulphonation melt | | | Sodium hydroxide solution | | Distilled $H_2O$ [ml] | Pressure hydrolysis | | | Yield % of the theoretical yield relative to | |
|---|---|---|---|---|---|---|---|---|---|---|---|
| | [g] | mols of BA* | % by weight of $H_2SO_4 + SO_3$ | mols | $C_{initial}$ [% by weight] | | [°C.] | pressure [bars] | time [h] | 3-SBA* | BA* |
| 5 a | 224 | 1 | 10.6** | 7.0 | 80 | Mixed under reflux | 290 | 22 | 4 | 98 | 91 |
| 5 b | 220 | 1 | 8.2*** | 6.4 | 70 | 49 | 290 | 22 | 4 | 98 | 91 |
| 5 c | 256 | 1 | 21.3**** | 8.0 | 80 | Mixed under reflux | 300 | 28 | 4 | 98 | 92 |
| 5 d | 256 | 1 | 21.3***** | 8.0 | 70 | 93 | 290 | 22 | 4 | 98 | 89 |
| 5 e | 210 | 1 | 3.5+ | 6.6 | 50 | 91 | 300 | 32 | 4 | 98 | 90 |
| 5 f | 210 | 1 | 3.5+ | 5.1 | 80 | Mixed under reflux | 290 | 22 | 4 | 97 | 88 |

*BA = benzoic acid; 3-SBA = 3-sulphobenzoic acid
**3-sulphobenzoic acid sulphonation mixture from Example 1
***3-sulphobenzoic acid sulphonation mixture from Example 2
****3-sulphobenzoic acid sulphonation mixture from Example 3
*****3-sulphobenzoic acid sulphonation mixture obtained as in Example 3, but by taking BA initially and adding 65% strength oleum
+3-sulphobenzoic acid sulphonation mixture from Example 4

EXAMPLE 6

1,900 g of 80% strength sodium hydroxide solution (=38 mols of NaOH) are taken in a 3 l nickel stirred autoclave at 240° C. and an autogenous pressure of 2 bars.

1,194 g (5.43 mols of benzoic acid employed) of the 3-sulphobenzoic acid from Example 2, in the form of a melt at 180° C., are pumped, in the course of 20 minutes, by means of a metering gear pump, under the surface of the sodium hydroxide solution, which is vigorously stirred. When the addition is complete, the temperature is increased to 289° C. and the pressure is 21 bars. Stirring is continued for a further 4 hours at 290° C. and the batch is diluted with a total of 3,000 ml of $H_2O$ and acidified to pH 1 with 37% strength HCl.

The product, which has been precipitated and filtered off at 20° C., is washed with a total of 1,200 ml of water and is dried. This gives 693 g of 98.5% pure 3-hydroxybenzoic acid=98% of the theoretical yield, relative to 3-sulphobenzoic acid, or 91% of the theoretical yield, relative to benzoic acid employed.

EXAMPLE 7

825 g of 80% strength sodium hydroxide solution (=16.5 mols of NaOH) are initially taken in a 1.3 l nickel autoclave at 330° C. and a pressure of 11 bars. Approximately 550 g (2.5 mols of benzoic acid employed) of the 3-sulphobenzoic acid from Example 2, in the form of a melt at 180° C., are injected in the course of 30 seconds, under a nitrogen pressure of 60 bars via a heated line, under the surface of the sodium hydroxide solution, which is vigorously stirred.

The temperature increases momentarily to 378° C., and the pressure to 59 bars. A subsequent analysis indicates that 84%=2.1 mols of the sulphonation melt are thereby caused to react. After a reaction time of 15 minutes to 370° C. and a pressure which rises to 65 bars, the conversion of the 3-sulphobenzoic acid is over 99%. The reaction mixture is cooled down and diluted by pumping in $H_2O$. It is worked up as in the preceding examples.

This gives 226 g of 98% pure 3-hydroxybenzoic acid=97% of the theoretical yield, relative to 3-sulphobenzoic acid injected, or 90% of the theoretical yield, relative to benzoic acid employed originally.

EXAMPLE 8

Molten technical 3-sulphobenzoic acid, at 180° C., which has been prepared from 12 mols of benzoic acid, 1.2 mols of $H_2SO_4$ and 13.2 mols of $SO_3$ (composition as in Example 2), and 75% strength sodium hydroxide solution, at 100° C., are pumped simultaneously into a flow tube from 2 stock vessels by means of 2 metering gear pumps, the delivery of which is adjusted so that 7 mols of NaOH, in the form of 75% strength sodium hydroxide solution, are delivered in relation to the quantity of sulphonation melt containing 1 mol of benzoic acid. The flow tube is made of nickel and has an internal diameter of 5 mm and a length of 500 mm. While flowing through the tube, the sulphonation melt and the sodium hydroxide solution have mixed completely with one another and have neutralized one another. The mixture passes at a temperature of 270° C. into a nickel autoclave in which 400 g of 50% strength sodium hydroxide solution (=5 mols of NaOH) have been placed at 210° C. and a pressure of 5 bars. During the addition, the pressure is limited to 7 bars by blowing off steam.

Pumping is discontinued after 6.4 mols of benzoic acid in the form of 3-sulphobenzoic acid melt and about 45 mols of sodium hydroxide solution have been pumped.

The final temperature in the nickel autoclave is 240° C. and the pressure is 7 bars.

The conversion of the 3-sulphobenzoic acid is complete after a pressure hydrolysis at 300° C. and 28 bars, lasting 4 hours. The mixture is worked up as in Examples 5 and 6.

This gives 803 g of 98% pure 3-hydroxybenzoic acid=89% of the theoretical yield, relative to benzoic acid employed.

EXAMPLE 9 (COMPARISON EXAMPLE)

Sulphonation: as described in Ann. Chem. 280, 6 (1894), with intermediate isolation in order to remove $H_2SO_4$; pressure hydrolysis: as described in U.S. Pat. No. 3,094,558, Example 3.

1,000 g of 20% strength oleum are added to 500 g of benzoic acid in the course of 10 minutes and the mixture is heated to 210° C. in the course of 120 minutes. After stirring for 4 hours, a sample dissolves completely in water and the reaction is therefore complete. A dark, nearly black melt is obtained. The crude mixture (1,456 g=97% of the total quantity of substances charged) contains the following, in addition to excess sulphuric acid:

| | | |
|---|---|---|
| 51.8% by weight of 3-sulphobenzoic acid | ≙ | 91.0% of the theoretical yield |
| 3.6% by weight of 4-sulphobenzoic acid | ≙ | 6.3% of the theoretical yield |
| 0.4% by weight of 2-sulphobenzoic acid | ≙ | 0.9% of the theoretical yield |
| 0.4% by weight of 3,5-disulphobenzoic acid | ≙ | 0.5% of the theoretical yield |
| 0.2% by weight of benzoic acid | ≙ | 0.6% of the theoretical yield |
| 0.04% by weight of benzophenone derivatives | ≙ | 0.1% of the theoretical yield |
| 0.3% by weight of diphenyl sulphone derivatives | ≙ | 0.7% of the theoretical yield |

The batch is diluted with 2,000 ml of $H_2O$ and 2,200 ml of saturated sodium chloride solution and an additional 66 g of NaCl are added. The precipitate is filtered off at room temperature, pressed down and washed with saturated NaCl solution. After drying, this gives 981 g of the Na salt of 3-sulphobenzoic acid containing 75.8% by weight of 3-sulphobenzoic acid (quoted as the free acid) (yield: the Na salt of 3-sulphobenzoic acid=89.7% of the theoretical yield, relative to benzoic acid).

296 g of the product isolated intermediately=1 mol of the Na salt of 3-sulphobenzoic acid, together with 200 g of NaOH and 67.5 g of $H_2O$ are heated at 300° C. for 5 hours 20 minutes in an Ni autoclave under the autogenous steam pressure and the mixture is worked up in the customary manner. This gives 129.6 g of 99% pure 3-hydroxybenzoic acid=94% of the theoretical yield, relative to 3-sulphobenzoic acid employed or 84% of the theoretical yield, relative to benzoic acid employed originally.

What is claimed is:

1. In a process for the preparation of 3-hydroxybenzoic acid by contacting 3-sulphobenzoic acid with an alkali metal hydroxide at an elevated temperature, the improvement which comprises:

(A) employing a technical 3-sulphobenzoic acid mixture containing sulphuric acid and/or sulphur trioxide, which technical mixture contains at least 75% by weight of 3-sulphobenzoic acid, relative to the total organic constituents present, and not more than 35% by weight of sulphuric acid and/or $SO_3$, relative to the total mass;

(B) the technical mixture is contacted with mixing at an elevated temperature with sufficient 50 to 100% strength by weight alkali metal hydroxide, the remaining 50 to 0% by weight consisting essentially of water, such that 2.5 to 8 mols of alkali metal hydroxide are present per mol of 3-sulphobenzoic acid, after neutralization of the sulphuric acid and all of the sulpho and carboxyl groups;

(C) the resultant alkaline reaction mixture is reacted at a temperature in the range of 220° to 450° C. under a pressure of 1 to 120 bars; and (D) the alkaline reaction mixture so obtained is acidified with a mineral acid to a pH value less than 4 and 3-hydroxy benzoic acid is recovered at a temperature in the range of $-5°$ to $+40°$ C.

2. A process according to claim 1, wherein the technical 3-sulphobenzoic acid mixture contains, relative to the total mass: 70 to 95% by weight of 3-sulphobenzoic acid, 2.5 to 7% by weight 4-sulphobenzoic acid, 0.5 to 1.5% by weight of 2-sulphobenzoic acid, 0.01 to 0.5% by weight of 3,5-disulphobenzoic acid, 0.01 to 1.5% by weight of diphenyl sulphone derivatives, 0.01 to 1.5% by weight of benzophenone derivatives and 2 to 20% by weight of $SO_3$ whether in the form of $SO_3$, $H_2SO_4$, or a mixture thereof.

3. A process according to claim 2, wherein the technical mixture is diluted with water in an amount up to equal parts prior to reaction with the alkali metal hydroxide.

4. A process for the preparation of 3-hydroxybenzoic acid which comprises:

(A) contacting benzoic acid with 0.01 to 0.5 mol of sulphuric acid per mol of benzoic acid and sulphonating the reaction mixture at an elevated temperature with 1 to 1.2 mols of $SO_3$ per mol of benzoic acid, the $SO_3$ being in the gaseous and/or liquid form and containing 0 to 35% by weight of sulphuric acid, relative to the $H_2SO_4$—$SO_3$ mixture, whereby to obtain a reaction mixture containing 3-sulphobenzoic acid;

(B) the reaction mixture so obtained containing 3-sulphobenzoic acid is thereafter contacted with sufficient 50 to 100% strength by weight alkali metal hydroxide, the remaining 50 to 0% by weight consisting essentially of water, such that 2.5 to 8 mols of alkali metal hydroxide are present per mol of 3-sulphobenzoic acid, after neutralization of the sulfuric acid and all the sulpho and carboxyl groups;

(C) the reaction mixture is reacted at a temperature in the range from 220° to 450° C. under a pressure of 1 to 120 bars; and (D) the reaction mixture so-obtained following the reaction of step C is acidified with a mineral acid to a pH less than 4 and 3-hydroxybenzoic acid is recovered at a temperature in a range from $-5°$ to $+40°$ C.

5. A process according to claim 4, wherein the benzoic acid/sulfuric acid mixture formed in step A is sulphonated with gaseous and/or liquid $SO_3$ which can contain 0 to 35% by weight of sulphuric acid, relative to the $H_2SO_4$—$SO_3$ mixture, at a temperature of 40° to 125° C., with the gaseous and/or liquid $SO_3$ being metered into the benzoic acid/sulphuric acid mixture at such temperature of 40° to 125° C. and thereafter the sulphonation is completed at a temperature of 125° to 170° C.

6. A process according to claim 4, wherein liquid $SO_3$ containing 0 to 35% by weight of sulphuric acid, relative to the sulphuric acid-$SO_3$ mixture, is employed as the sulphonating agent, benzoic acid/sulphuric acid mixture is metered into the liquid $SO_3$ at a temperature of 40° to 125° C. and, thereafter, the sulphonation is completed at a temperature of 125° to 170° C.

7. A process according to claim 1, wherein after mixing the reaction mixture containing the 3-sulphobenzoic acid with the alkali metal hydroxide, water is removed from that resultant reaction mixture by distillation.

8. A process according to claim 7, wherein the reaction of 3-sulphobenzoic acid with alkali metal hydroxide is effected at normal pressure.

9. A process according to claim 1, wherein the reaction of 3-sulphobenzoic acid with alkali metal hydroxide is effected at normal pressure and during the reaction, water is distilled off.

10. A process according to claim 4, wherein after mixing the 3-sulphobenzoic acid mixture with alkali metal hydroxide, water is removed by distillation.

11. A process according to claim 10, wherein the 3-sulphobenzoic acid mixture is mixed with the alkali metal hydroxide at normal pressure.

12. A process according to claim 4, wherein the 3-sulphobenzoic acid mixture is mixed with alkali-metal hydroxide at normal pressure and during the mixing water is distilled off.

13. A process according to claim 1, wherein 3-sulphobenzoic acid is mixed with an alkali metal hydroxide in a closed reactor in order to maintain the pressure which is formed as a result of the resultant mixing.

14. A process according to claim 4, wherein the 3-sulphobenzoic acid mixture is mixed with alkali metal hydroxide in a closed reactor in order to maintain the pressure formed as a result of the mixing.

15. A process according to claim 13, wherein said reactor is in the form of a mixing tube.

16. A process according to claim 14, wherein said reactor is in the form of a mixing tube.

17. A process according to claim 1, wherein the alkaline reaction mixture which results from contact of the 3-sulphobenzoic acid with an alkali metal hydroxide is pressure-hydrolyzed employing the autogenous steam pressure of the system or a partial steam pressure of about 5 to 80 bars.

18. A process according to claim 4, wherein the alkaline reaction mixture which results from contact of the 3-sulphobenzoic acid with an alkali metal hydroxide is pressure-hydrolyzed employing the autogenous steam pressure of the system or a partial steam pressure of about 5 to 80 bars.

19. A process according to claim 17, wherein the mixture which results from the partial hydrolysis is contacted with a mineral acid to adjust its pH to a value of about 0 to 4 and the mixture is diluted with a sufficient amount of water to dissolve inorganic salts present therein.

20. A process according to claim 18, wherein the mixture which results from the partial hydrolysis is contacted with a mineral acid to adjust its pH to a value of about 0 to 4 and the mixture is diluted with a sufficient amount of water to dissolve inorganic salts present therein.

21. A process according to claim 4, wherein the 3-sulphobenzoic acid containing mixture subjected to contact with the alkali metal hydroxide contains 64 to 93% by weight of 3-sulphobenzoic acid and not more than 35% by weight of sulphuric acid/sulphur trioxide mixture.

22. A process according to claim 21, wherein said 3-sulphobenzoic acid containing reaction mixture contains not more than 25% by weight of the mixture of sulphuric acid and sulphur trioxide.

23. A process according to claim 22, wherein said 3-sulphobenzoic acid containing mixture contains less than 15% by weight of sulphuric acid/sulphur trioxide.

24. A process according to claim 4, wherein the 3-sulphobenzoic acid containing reaction mixture which is contacted with the alkali metal hydroxide itself contains 88 to 95% by weight 3-sulphobenzoic acid, 4–7% by weight 4-sulphobenzoic acid, 0.1 to 1.5% by weight 2-sulphobenzoic acid, 0.01–0.05 3,5-disulphobenzoic acid, 0.01–1.5% by weight benzophenone derivatives and 0.01–1.5% by weight diphenyl sulphone derivatives.

25. A process according to claim 1, wherein the process is carried out without isolation of any intermediate alkali metal salt of 3-sulphobenzoic acid.

26. A process according to claim 4, wherein the process is carried out without isolation of any intermediate alkali metal salt of 3-sulphobenzoic acid.

27. A process according to claim 1, wherein the process is carried out without any intermediate removal of sulphuric acid.

28. A process according to claim 4, wherein the process is carried out without any intermediate removal of sulfuric acid.

* * * * *